US004001558B2

United States Statutory Invention Registration [19]

[11] Reg. Number: H1558

[45] Published: Jul. 2, 1996

Goulait et al.

[54] METHOD FOR MANUFACTURING AND AN ABSORBENT ARTICLE HAVING ELASTICALLY EXTENSIBLE PORTIONS

[76] Inventors: David J. K. Goulait, 6100 Center Hill Rd., Cincinnati, Ohio 45224; Jerry E. Carstens, 1001 Tillman Ave., Memphis, Tenn. 38112

[21] Appl. No.: 109,014

[22] Filed: Aug. 18, 1993

Related U.S. Application Data

[60] Division of Ser. No. 821,654, Jan. 16, 1992, which is a continuation-in-part of Ser. No. 382,516, Jul. 19, 1989, abandoned, which is a continuation-in-part of Ser. No. 64,896, Jun. 19, 1987, Pat. No. 4,854,984.

[51] Int. Cl.[6] ..... B31F 1/20

[52] U.S. Cl. ..... 156/210; 156/290; 156/292; 156/462

[58] Field of Search ..... 156/163, 164, 156/201, 200, 210, 229, 292, 462, 461, 470–472, 494; 604/385.1, 385.2, 389

[56] References Cited

U.S. PATENT DOCUMENTS

| | | | |
|---|---|---|---|
| 2,193,052 | 3/1940 | Atwater . | |
| 2,547,880 | 4/1951 | Meyer et al. . | |
| 2,978,006 | 4/1961 | Clemens . | |
| 3,425,888 | 2/1969 | Kellicutt . | |
| 3,530,023 | 9/1970 | Schutte et al. . | |
| 4,116,892 | 9/1978 | Schwarz . | |
| 4,223,059 | 9/1980 | Schwarz . | |
| 4,227,531 | 10/1980 | McLeod | 604/385.2 |
| 4,285,747 | 8/1981 | Rega | 156/164 |
| 4,377,431 | 3/1983 | Chodosh . | |
| 4,397,704 | 8/1983 | Frick | 156/462 X |
| 4,515,595 | 5/1985 | Kievit et al. | 604/385.2 |
| 4,517,714 | 5/1985 | Sneed et al. . | |
| 4,582,550 | 4/1986 | Sigl | 156/85 X |
| 4,806,300 | 2/1989 | Walton et al. . | |
| 4,808,252 | 2/1989 | Lash | 156/73.1 |
| 4,854,984 | 8/1989 | Ball et al. . | |
| 4,857,067 | 8/1989 | Wood et al. . | |
| 4,859,169 | 8/1989 | Walton et al. . | |
| 4,919,738 | 4/1990 | Ball et al. . | |
| 4,968,313 | 11/1990 | Sabee | 604/384 |
| 4,978,570 | 12/1990 | Heyn et al. . | |

FOREIGN PATENT DOCUMENTS

| | | |
|---|---|---|
| 0295957 | 12/1988 | European Pat. Off. . |
| 2088069 | 1/1972 | France . |

*Primary Examiner*—Charles T. Jordan
*Assistant Examiner*—J. R. Hardeo

[57] ABSTRACT

A method for forming a disposable absorbent article having portions which are elastically extensible in at least the cross-machine direction. The method generally comprises the steps of providing a chassis comprising: a liquid pervious topsheet, a liquid impervious backsheet joined with said topsheet, and an absorbent core positioned between said topsheet and said backsheet; providing a first lamina, said first lamina being joined to said chassis and having pleats, said pleats being oriented in a second direction; providing at least one elastomeric lamina in face to face relation with at least a portion of said first lamina; providing two circumferentially grooved rolls, a first roll and a second roll, having mutually parallel axes and defining a nip therebetween, at least said first roll having a plurality of circumferential grooves and lands intermediate said grooves, said grooves being oriented in said second direction; passing said first lamina and said elastomeric lamina in face to face relation through said nip, such that said pleats of said first lamina face said grooves of said first roll; transversely registering the pleats of said first lamina with said grooves of said first roll; pressing said rolls together about the plane generally perpendicular to and connecting the axes of said rolls so that said first lamina contacts said elastomeric lamina at a position corresponding to said lands; and bonding said first lamina to said elastomeric lamina at said positions of contact.

15 Claims, 7 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR MANUFACTURING AND AN ABSORBENT ARTICLE HAVING ELASTICALLY EXTENSIBLE PORTIONS

This is a division of application Ser. No. 07/821,654 filed on Jan. 16, 1992, which is a continuation-in-part of application Ser. No. 07/382,516, filed Jul. 19, 1989, and entitled "Improved Method For Manufacturing A Laminate Having At Least One Pleated Lamina", now abandoned which is a continuation-in-part of application Ser. No. 64,896, filed on Jun. 19, 1987, now U.S. Pat. No. 4,854,984.

TECHNICAL FIELD

The present invention relates to a method of manufacturing an elastomeric laminate using an apparatus having at least one circumferentially grooved roll. More particularly the invention relates to a method of manufacturing a disposable absorbent article comprising such a laminate.

BACKGROUND OF THE INVENTION

Laminates having at least one pleated lamina are known in the prior art. For example, U.S. Pat. No. 4,377,431, issued Mar. 22, 1983, to Chodosh teaches a fabric having three substantially coextensive laminae, one lamina of which is pleated. The prior art also teaches the use of rolls 22 and 24 having circumferential grooves and lands to impart lateral stretch to a lamina, as, for example, shown by U.S. Pat. No. 4,517,714, issued May 21, 1985, to Sneed et al. However, the prior art does not show a method to join at least two laminae in face to face relation, at least one lamina being pleated, to form elastically extensible portions of a disposable absorbent article.

Infants and other incontinent individuals wear disposable absorbent articles such as diapers, incontinent briefs, diaper holders, and the like, to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. Re. No. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions for Disposable Diaper" issued to Buell on Jan. 14, 1975, describes an elasticized leg cuff disposable diaper which has achieved wide acceptance and commercial success.

However, the prior art does not show a method of making a disposable absorbent article having elastically extensible portions which are made by passing an unpleated, elastically extensible lamina and at least one pleated lamina in face to face relation through the nip formed by a pair of rolls, at least one of the rolls being circumferentially grooved.

Therefore, it is an object of this invention to provide a method of manufacturing a disposable absorbent article having elastically extensible portions which are made by passing an unpleated, elastically extensible lamina and at least one pleated lamina in face to face relation through the nip formed by a pair of rolls, at least one of the rolls being circumferentially grooved.

It is a still further object of the present invention to provide a disposable absorbent article having elastically extensible portions which are made by passing an unpleated, elastically extensible lamina and at least one pleated lamina in face to face relation through the nip formed by a pair of rolls, at least one of the rolls being circumferentially grooved.

These and other objects of the present invention will be more readily apparent when considered in reference to the following description and when taken in connection with the accompanying drawings.

SUMMARY OF THE INVENTION

The present invention relates to a method for forming a disposable absorbent article having portions which are elastically extensible in at least the cross-machine direction. The method comprises the steps of:

providing a chassis, said chassis comprising:

a liquid pervious topsheet, a liquid impervious backsheet associated with said topsheet, an absorbent core positioned between said topsheet and said backsheet;

providing a first lamina, said first lamina being joined to said chassis and having pleats, said pleats being oriented in a second direction;

providing at least one elastomeric lamina in face to face relation with at least a portion of said first lamina;

providing two circumferentially grooved rolls, a first roll and a second roll, having mutually parallel axes and defining a nip therebetween, at least said first roll having a plurality of circumferential grooves and lands intermediate said grooves, said grooves being oriented in said second direction;

passing said first lamina and said elastomeric lamina in face to face relation through said nip, such that said pleats of said first lamina face said grooves of said first roll;

transversely registering the pleats of said first lamina with said grooves of said first roll;

pressing said rolls together about the plane generally perpendicular to and connecting the axes of said rolls so that said first lamina contacts said elastomeric lamina at a position corresponding to said lands; and bonding said first lamina to said elastomeric lamina at said positions of contact.

In one execution, an elastomeric lamina and pleated lamina may be provided and joined in face to face relation by passing the laminae through the nip defined by a smooth roll and a grooved roll with the pleats of the pleated lamina facing and transversely registered with the grooves of the grooved roll. In a second execution, two pleated laminae are joined to an elastomeric lamina by passing the laminae through the nip defined by two circumferentially grooved rolls with the pleats of the pleated laminae each facing and transversely registered in the grooves of the grooved rolls and with the elastomeric lamina positioned between the pleated laminae.

BRIEF DESCRIPTION OF THE DRAWINGS

While the Specification concludes with claims particularly pointing and distinctly claiming the present invention, it is believed the same will be better understood by the following description taken in conjunction with the accompanying drawings in which like parts are designated by the same reference numeral, related or analogous parts are designated with a prime symbol and:

DETAILED DESCRIPTION OF THE INVENTION

Figure 1:
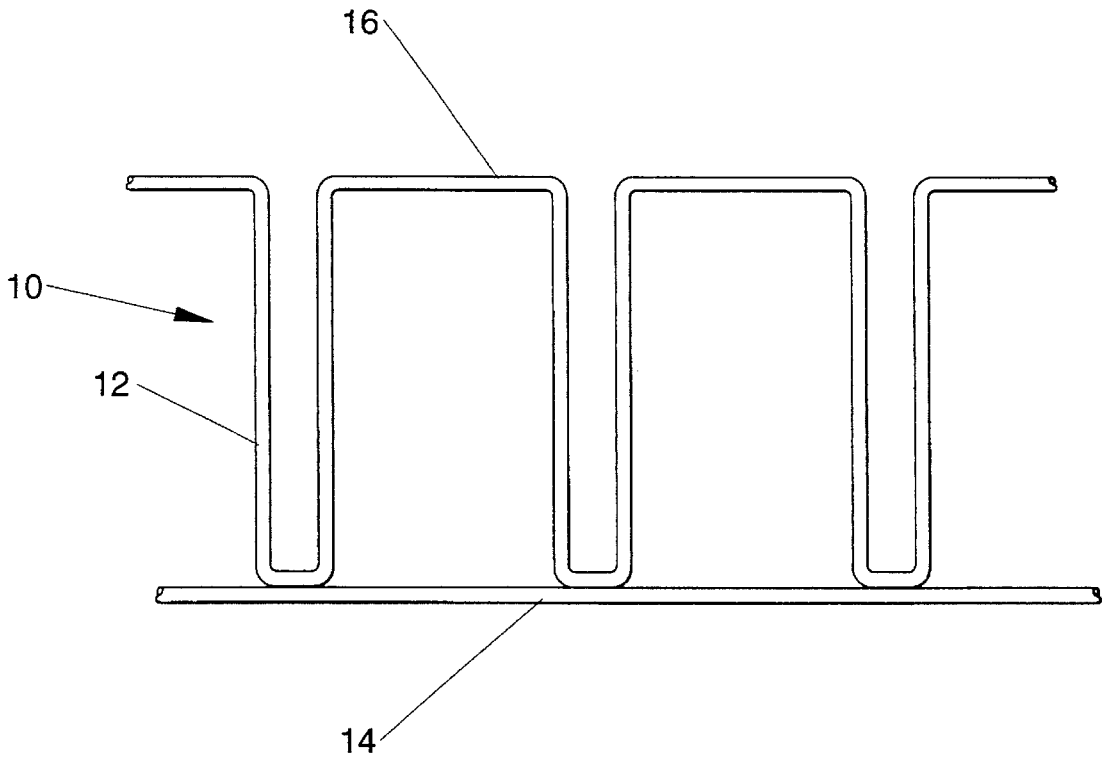
FIG. 1 is a vertical sectional view of a laminate produced according to the present invention and having one pleated lamina and one unpleated lamina.
Figure 2:
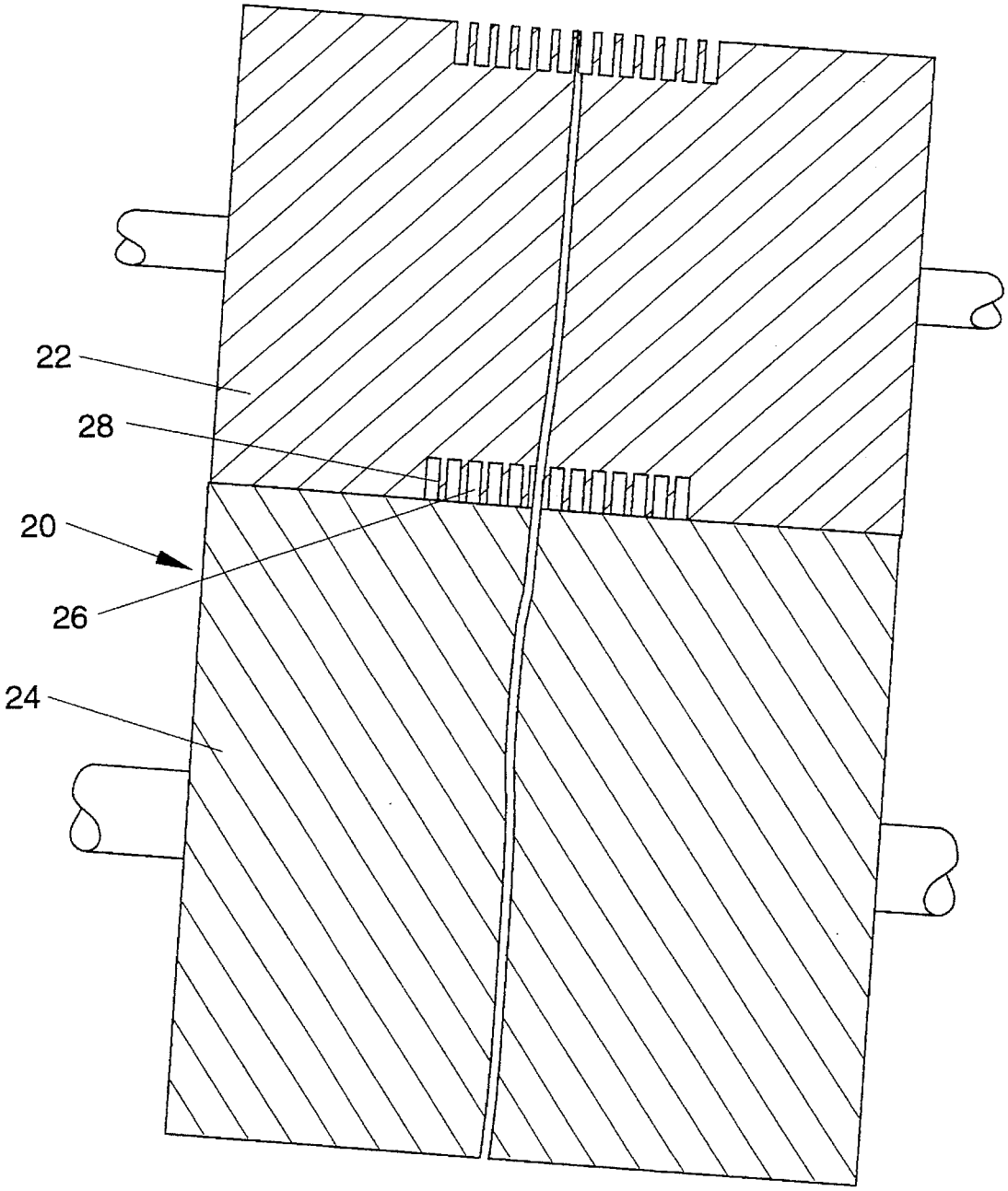
FIG. 2 is a vertical sectional view of an apparatus used to produce the laminate of FIG. 1, as viewed in the machine direction.

The present invention is directed to joining two laminae in face to face relation to produce a unitary, elastomeric laminate 10, as illustrated in FIG. 1. The laminate 10 may also be referred to, herein, as the stretch laminate. The first lamina 12 of the laminate 10 is pleated with pleats 16 oriented in the machine direction. The first lamina 12 may also be referred to, herein, as the pleated lamina. The second lamina 14 is elastomeric and is unpleated. The second lamina 14 may also be referred to, herein, as the unpleated lamina or the elastomeric lamina. The laminate 10 may be produced with the apparatus 20 illustrated by FIG. 2. The apparatus 20 comprises two rolls 22 and 24 and the nip defined therebetween.

Preferably, the rolls 22 and 24 have generally straight axes, although rolls 22 and 24 having curved axes (not shown) may be used with the present invention as well. The rolls 22 and 24 are disposed and rigidly held by a frame (not shown) as is commonly known in the art, so that the axes of the rolls 22 and 24 are mutually parallel. The frame may support both ends of the rolls 22 and 24, or the rolls 22 and 24 may be cantilevered from one end.

The first roll 22 is circumferentially grooved and the second roll 24 has a generally smooth, uninterrupted circumference. As used herein, the term "groove" refers to a channel in the roll 22, which channel extends substantially around the circumference of the roll 22. The bottom of the groove 26 is that face of the groove 26 which is of the least diameter. The sides of the groove 26 are those faces radially oriented and which extend from the bottom of the groove 26 to the outer circumference of the roll 22. The groove 26 may be of any suitable cross section, although a rectangular cross section, as shown, is generally preferred.

Figure 3:
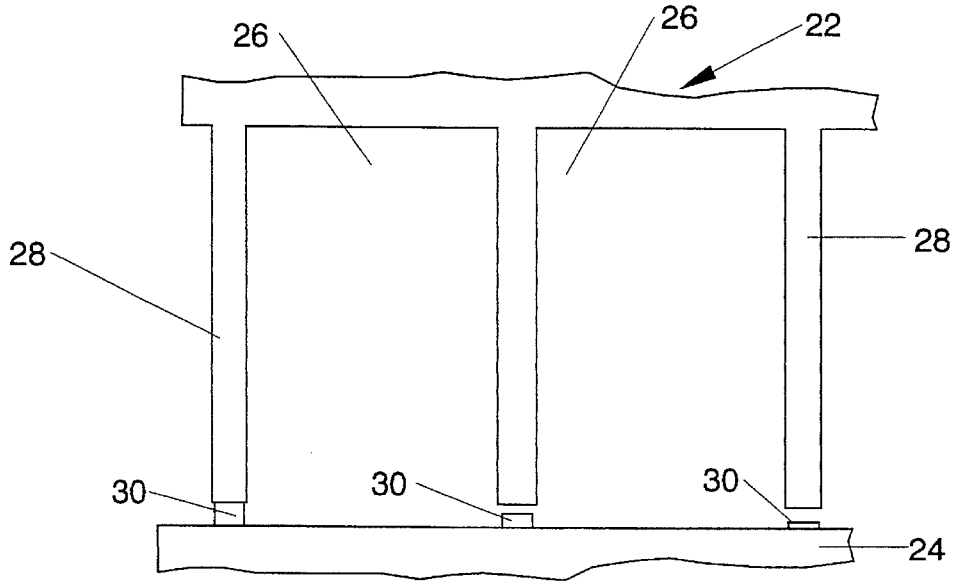
FIG. 3 is an enlarged view of a portion of the apparatus of FIG. 2, showing the grooves and lands.

As illustrated in FIG. 3, intermediate the grooves are lands 28. As used herein, the phrase "land" refers to any portion of the roll 22 intermediate two grooves 26 and which has a diameter greater than that than of the bottom of either adjacent groove 26. Each land 28 may be thought of as an annular cantilevered beam having a fixed end at the bottom of the grooves 26 and a free end at the outer circumference of the roll 22. It is not necessary that the land 28 be of constant diameter throughout the entire circumference. It is only necessary that the space between the grooves 26 be interrupted in diameter and that the grooves 26 are not contiguous. As used herein the "depth" of the groove 26 is the difference between the radius at the bottom of the groove 26 and the greatest radius of the outermost portion of the adjacent land 28. As used herein the term "pitch" refers to the distance, taken parallel to the axis of the roll 22, between the circumferential centerlines of adjacent grooves 26, or the distance between centerlines of adjacent pleats 16 of the pleated lamina 12.

Disposed on the distal end of the land 28 of the grooved roll 22 or on the periphery of the smooth roll 24 and registered with the lands 28 of the grooved roll 22 may be one or more generally radially oriented upstanding protrusions 30. The upstanding protrusions 30 may be generally cylindrically or rectangularly shaped, and provide discrete bonding points for the laminae 12 and 14 passing through the nip. The protrusions 30 have a height of about 0.5 millimeters (0.020 inches) and a diameter of about 0.5 millimeters to about 1.4 millimeters (0.20 inches). The rolls 22 and 24 are pressed together to effect joining the laminae 12 and 14. The protrusions 30 provide sites of increased compressive pressure, so that a more stable bond is obtained. Preferably, the protrusions 30 are not circumferentially registered, so that the bonding sights are transversely staggered on the resulting laminate 10.

The diameters of the rolls 22 and 24 are controlled by the compressive force used to urge the rolls 22 and 24 together and the length of the rolls 22 and 24. As either parameter increases, the minimum diameter of the grooved roll 22 (measured at the bottom of the grooves 26) must increase accordingly. The diameter of the roll 22 at the outer periphery of the lands 28 is then selected in accordance with the desired pleat height. The diameter of the second roll 24 is preferably different from, but no less than, the minimum diameter of the grooved roll 22 - so that adequate strength is maintained, but the same points on the circumferences of the rolls 22 and 24 do not contact on each revolution. Generally as the difference between the diameter of the roll 22 at the bottom of the grooves 26 and the diameter at the circumference of the lands 28 increases, the lands 28 should be made wider to provide adequate strength and to preclude axial movement of the distal ends of the lands 28.

The width and pitch of the grooves 26 of the grooved roll 22 should correspond generally to the width and pitch of the pleats 16 of the pleated lamina 12. For pleats having a pitch less than about 0.17 inches, the grooves 26 may be about 10 percent wider than the desired pleats 16 to allow for variations in tracking and volume of the pleated lamina 12. Further, the grooves 26 should have a depth sufficient to accommodate the size of the pleats 16, otherwise wrinkling of the pleated lamina 12 may occur.

Pleat sizes ranging in height from about 0.8 millimeters to about 6.4 centimeters (0.03 inches to 0.75 inches) and grooves 26 having a pitch ranging from about 2.5 millimeters to 13 millimeters (0.10 inches to 0.50 inches) work well with the method disclosed herein. Thus the grooves 26 may advantageously be made of any size within this range, or of other sizes and geometries as desired.

The second roll 24 is relatively smooth, being ungrooved, corresponding to the second lamina 14 of the laminate 10. Generally as the force compressing the first and second rolls 22 and 24 increases, or the length of the rolls 22 and 24 increases, a larger diameter second roll 24 is desired. Alternatively, the second 24 roll may be slightly bowed towards the first 22 roll so that constant surface interface is maintained between the rolls 22 and 24.

Each roll 22 and 24 is free to rotate about its respective axis. The rolls 22 and 24 rotate in the opposite sense - so the circumferences of the rolls 22 and 24 are traveling in substantially the same direction at the nip. Preferably, both rolls 22 and 24 are externally driven, particularly as higher processing velocities are utilized. Alternatively, the first roll 22 may be externally driven, and the second roll 24 rotated by the tangential frictional component of the laminae 12 and 14 passing through the nip. The laminae 12 and 14 may pass through nip at a velocity of about 120 to about 310 meters per minute (400 to 1,000 feet per minute). For speeds of about 120 meters per minute, or greater, a motor of about 7500 watts for each roll 22 and 24 is suitable. It is not, however, necessary that the surface velocity of the rolls 22 and 24 be matched.

The laminae 12 and 14 are held in face to face relation and pass through the nip in the machine direction. As used herein, the term "machine direction" refers to that direction generally perpendicular to both axes of the rolls 22 and 24 and the plane which connects the axes of the rolls 22 and 24. Furthermore, as used herein, the term "cross machine direction" refers to the direction generally parallel to the axes of the rolls 22 and 24 and perpendicular to the machine direction. The "nip plane" is that plane generally perpendicular to the plane which connects the axes of the rolls 22 and 24 and which intercepts the nip of the rolls 22 and 24.

The laminae 12 and 14 may be composed of any material suitable for the end-use application. Generally, as the thickness of the pleated lamina 12 increases, the pitch of the grooves 26 should increase to accommodate the greater amount of material present. The process described herein is successfully used with elastomeric, paper and polyolefinic laminae 12 and 14, such as polypropylene and polyethylene. The pleated lamina 12 may have a thickness ranging from about 0.02 millimeters to about 0.5 millimeters (0.0008 inches to 0.02 inches). The pleated lamina 12 may be either a film or a nonwoven material. The unpleated lamina 14 may be elastomeric. The unpleated lamina 14 may be a nonwoven material, but i s preferably a film.

The first lamina 12 is pleated, using any means well known in the art for providing "pleats", i.e. portions displaced from the plane of the lamina 12, which pleats are oriented substantially parallel to the machine direction. Suitable pleating methods are disclosed in U.S. Pat. No. 4,252,591, issued Feb. 24, 1981 to Rosenburg, and Canadian Pat. 758,794, issued May 16, 1967 to Ives et al., which patents are incorporated herein by reference for the purpose of showing suitable methods to provide machine direction oriented pleats. The second lamina 14 is used in a relatively smooth, unpleated condition.

The laminae 12 and 14 are preferably supplied from individual supply rolls 22 and 24 (not shown). Each supply roll is mounted with its respective axis generally parallel that of the rolls 22 and 24 and upstream of the nip. The laminae 12 and 14 are brought together in face to face relation either by using tracking rolls (not shown) or directly through the nip of the rolls 22 and 24. The laminae 12 and 14 may be pulled through the nip by takeup rolls 22 and 24 (not shown). The laminae 12 and 14 may pass through the nip at the same surface velocity or, if desired, at a different surface velocity, The pleated lamina 12 is transversely registered with the grooves 26 so that preferably the centerline of each pleat 16 is aligned with the centerline of each groove 26. This may be accomplished by transversely adjusting the position of the supply roll, or the position of the last roll which the pleated lamina 12 crosses, relative to the position of the grooved roll 22. Such adjustment may be accomplished by axial movement of either the supply roll or the grooved roll 22. It is important that the pleated lamina 12 travel through the nip in a direction parallel to the machine direction, otherwise wrinkling and bunching of the lamina 12 within the grooves 26 and at the nip may result. Therefore, the axis of the supply over for the pleated lamina 12 should be generally parallel to the nip.

It is important that the pleated lamina 12 not become wrinkled or transversely misregistered with the grooves 26 of the grooved roll 22. If this occurs, the pleats 16 may become laterally tensioned and a laminate 10 of uniform pitch and the desired aesthetics may not result. Typically, if the pleats 16 should become laterally tensioned (e.g. due to a geometry mismatch with the grooves 26 of the first roll 22 or not being registered with the grooves 26) a relatively large pleat 16 will result at the point the pleated lamina 12 was tensioned and a relatively small pleat 16 will result elsewhere, due to the relative loss and transfer of material necessary to form the larger pleat 16.

The position of the unpleated lamina 14 relative to the nip is not critical. It is only necessary that the transverse ends of the laminae 12 and 14 be coterminous, otherwise the resulting laminate 10 will have a single lamina at each edge. Although it is not critical, the unpleated lamina 14 should pass through the nip generally parallel to the machine direction, otherwise the unpleated lamina 14 may not be properly joined to the pleated lamina 12.

The confluent laminae 12 and 14 are joined at the nip or after passing through the nip. The laminae 12 and 14 may be joined by adhesive or autogenous bonding. If adhesive bonding is selected, the adhesive is applied to the face of either lamina 12 or 14 which is oriented towards the other lamina 12 or 14. Preferably the adhesive will be applied to the unpleated lamina 14. Alternatively, an adhesive lamina (not shown) may be interposed between the pleated 12 and unpleated lamina 14 so that a laminate 10 having three laminae is formed; with a central lamina of adhesive and two outboard laminae 12 and 14, one pleated, one unpleated, as described above. One suitable method for producing such a three laminae laminate 10 is disclosed in U.S. Pat. No. 4,377,431 issued Mar. 22, 1983, to Chodosh and incorporated herein by reference for the purpose of showing how to produce such a laminate 10. Pressure sensitive adhesive marketed by The Century Adhesives Company of Columbus, Ohio as a diaper chassis adhesive has been found to work well for adhesive joining of the laminae 12 and 14.

Alternatively, a three (or more) laminae laminate 10 having a nonadhesive central lamina may be formed. If a nonadhesive central lamina is selected, the three (or more) laminae may be joined by autogenous bonding.

If autogenous bonding is selected, it may be accomplished by heating the rolls 22 and 24 and pressing the rolls 22 and 24 together about the plane generally perpendicular to and connecting the axes of the rolls 22 and 24. Additionally, the laminae 12 and 14 may be drawn through the nip at a differential velocity of about 2% to about 40% of the velocity of the lamina 12 or 14 having the lower velocity at the plane of the nip. Autogenous bonding, as described in U.S. Pat. No. 4,854,984, issued to Ball et al. on Aug. 8, 1989, has been found suitable, which application is incorporated herein by reference for the purpose of showing a particularly preferred method of autogenous bonding.

The rolls 22 and 24 may be pressed together so that a pressure of about 42,200,000 to about 56,200,000 kilograms per square meter (60,000 to 80,000 pounds per square inch) is obtained and the laminae 12 and 14 are brought into contacting relationship at the positions of the lands 28. The pressure is measured by dividing the compressive force applied to the rolls 22 and 24 by the area of the protrusions 30 at the bonding footprint. The bonding footprint is obtained by inserting an unpleated stationary lamina 14 between the rolls 22 and 24 and compressing the rolls 22 and 24 with a known force until an impression on the lamina 14 is obtained from each protrusion in the vicinity of the nip. The area of each protrusion and the number of impressions are counted and summed to yield the effective bonding area. This area is divided into the applied force to yield the compressive pressure on the roll 22 or 24 having the protrusions 30.

A nonlimiting example of the process disclosed herein found suitable for producing a laminate 10 having two laminae 12 and 14, one pleated, one unpleated is as follows. A first lamina 12 having pleats of about 9.5 millimeters (0.38 inches) height, about 4.7 millimeters (0.19 inches) width, and a pitch of about 6.4 millimeters (0.25 inches) is provided. The second lamina 14 is unpleated and generally smooth. Both laminae 12 and 14 are made of a thermoplastic material, particularly polypropylene. The first lamina 12 is a polypropylene nonwoven material of about 2.2 denier and a basis weight of about 24 grams per square meter (20 grams per square yard). The second lamina 14 is a polypropylene film having a thickness of about 0.2 millimeters (0.008 inches).

Two rolls 22 and 24 are provided. The first roll 22 is grooved, with grooves 26 of about 9.5 millimeters (0.38 inches) in depth, about 4.7 millimeters (0.19 inches) in width and of about 6.4 millimeters (0.25 inches) in pitch. The maximum diameter of the roll 22 is about 15.2 centimeters (6 inches) and the diameter at the bottom 26 of the grooves is about 14.0 centimeters (5.5 inches). The second roll 24 is not grooved and has a diameter of about 29 centimeters (11.4 inches). Both rolls 22 and 24 have straight and mutually parallel axes, and are about 33 centimeters (13 inches) long.

The second roll 24 has 36 equally spaced protrusions 30 corresponding to the axial position of each land. Each protrusion 30 is about 3.8 millimeters (0.015 inches) in radial dimension and has a parallelogram shaped surface of about 1.9 square millimeters (0.003 square inches). The rolls 22 and 24 are pressed together with a force of about 2500 kilograms (5600 pounds), so that a pressure of about 49,200,000 kilograms per square meter (70,000 pounds per square inch) is obtained on the raised protrusions 30 of the circumferentially grooved roll 22.

The laminae 12 and 14 are drawn through the nip defined by the rolls 22 and 24 at a uniform and constant velocity of about 180 meters per minute (600 feet per minute). Both rolls 22 and 24 are heated to a surface temperature of about 82° C. to provide for autogenous bonding of the laminae 12 and 14. The resulting laminate 10 has pleats 16 of generally uniform pitch, height, and width.

Figure 4:
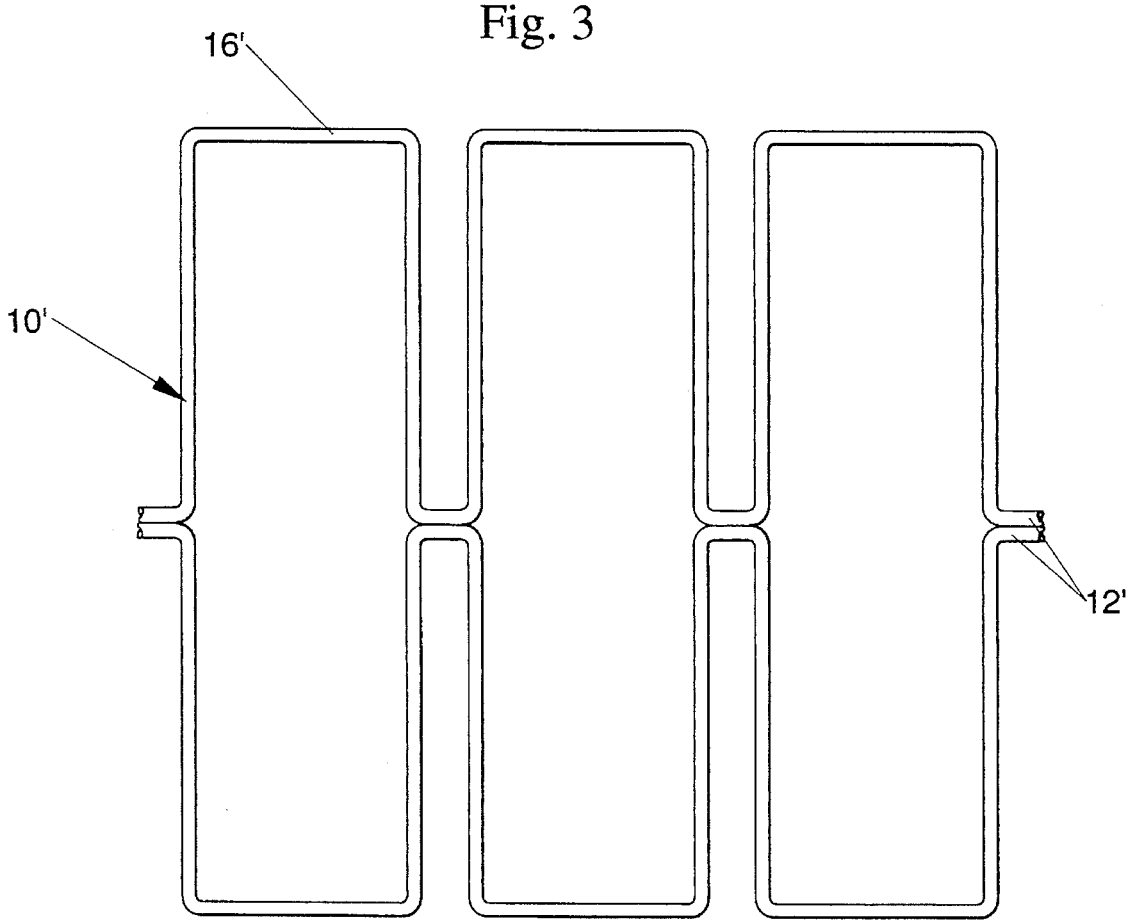
FIG. 4 is a vertical sectional view of a laminate produce according to the present invention and having two pleated laminae.
Figure 5:
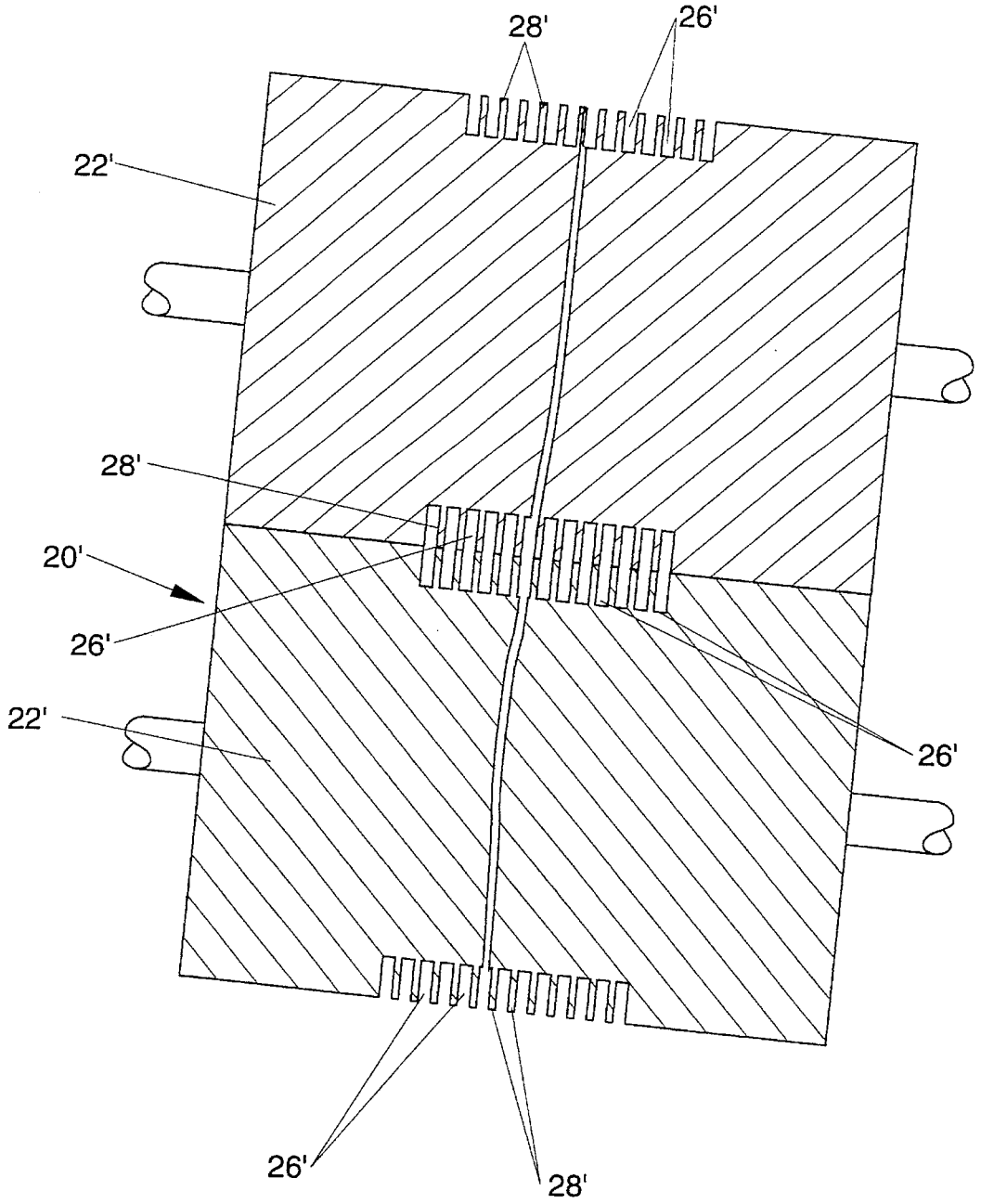
FIG. 5 is a vertical sectional view of an apparatus used to produce the laminate of FIG. 4, as viewed in the machine direction.

Variations in the disclosed method of producing a pleated laminate 10 are feasible. For example, as shown in FIG. 4, a laminate 10 having two pleated laminae 12', each with oppositely facing machine direction oriented pleats 16' can be produced by the method described herein. Referring to FIG. 5, to produce such a laminate 10', it is only necessary two grooved rolls 22' and the nip defined therebetween, be provided, and that at least two, and preferably more, of the lands 28' of the grooved rolls 22' be transversely registered.

Two laminae 12' having longitudinal pleats made of either the same or different materials, and formed as described above, are provided and confluently passed through the nip in face to face relation with the pleated surfaces of the laminae 12' facing outwardly and oppositely from each other. The pleats 16' of the laminae 12' are matched in geometry to the circumferential grooves 26' of the rolls 22' and transversely registered as described above. The laminae 12' are then joined, either adhesively or autogenously as described above.

Figure 6:
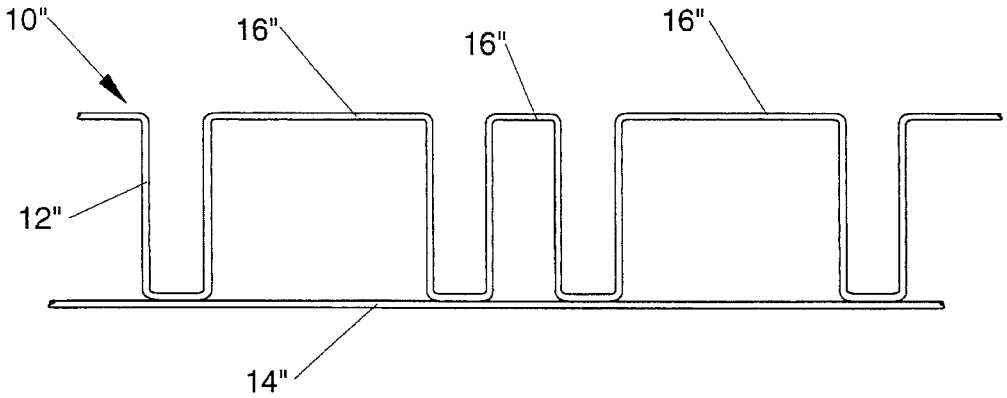
FIG. 6 is a vertical sectional view of a laminate produce according to the present invention having one pleated lamina of nonuniform pitch.
Figure 7:
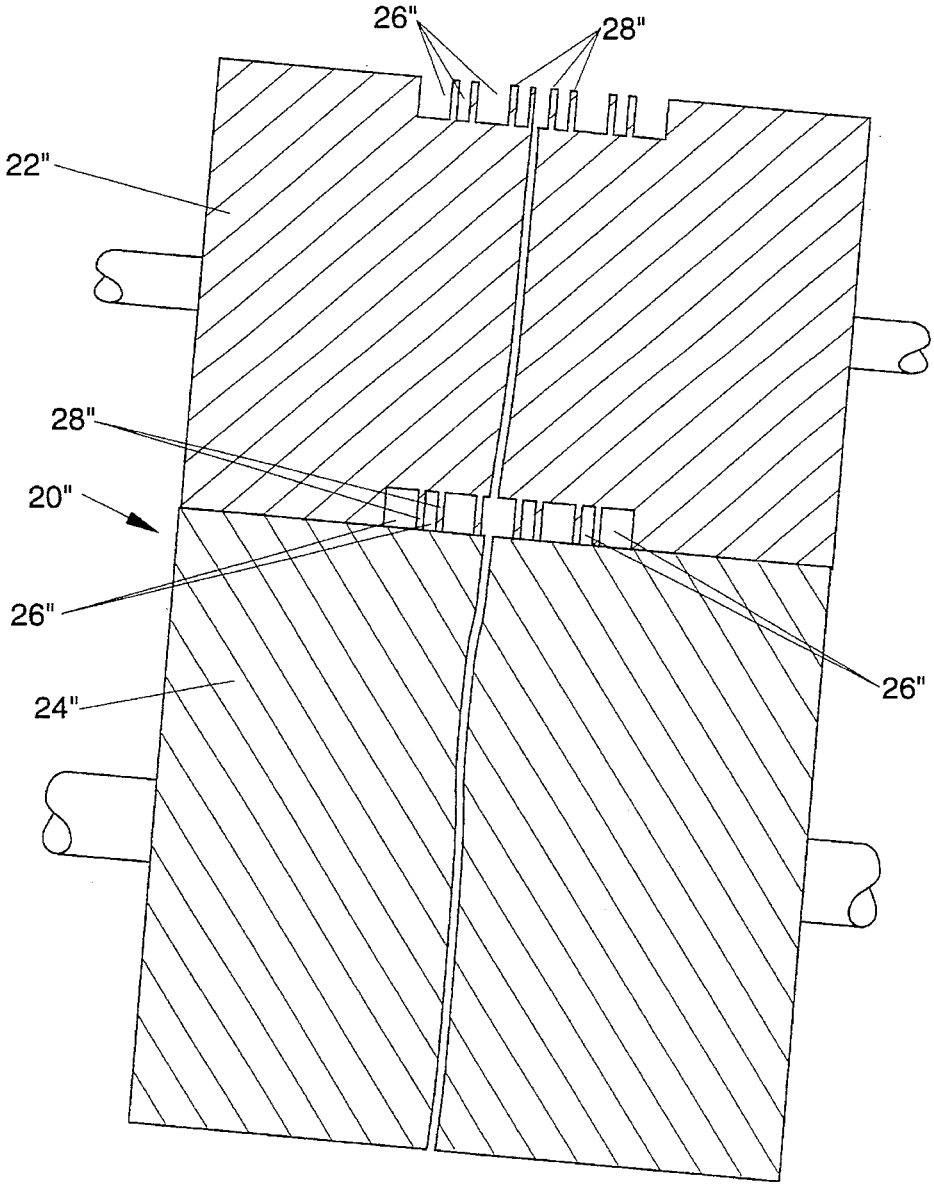
FIG. 7 is a vertical sectional view of an apparatus used to produce the laminate of FIG. 6, as viewed in the machine direction.

In another variation of the method of making the first above-described laminate 10, a laminate 10" having a pleated lamina 12" of nonuniform pitch, and a unpleated lamina 14" results, as illustrated in FIG. 6. Referring to FIG. 7, to produce such a laminate 10", a circumferentially grooved roll 22" having a nonuniform pitch, i.e. the spacing between adjacent grooves 26" varies along the axial length of the roll 22", is provided. A roll 24" which is not grooved is also provided. A first lamina 14" is provided, having pleats 16" of nonuniform pitch, corresponding to the width and pitch of the grooves 26" of the first roll 22". The first lamina 12" and a second unpleated lamina 14" are confluently passed through the nip in face to face relation as described above. This process yields a laminate 10" having one lamina 12" with spaced pleats 16" of a nonuniform and variable pitch and one unpleated lamina 14". Thus, the grooves 26" of the grooved roll 22" may either be spaced on a uniform pitch or on a nonuniform pitch.

It will be apparent to one skilled in the art, that the two variations described above may be combined to produce a laminate 10' having two laminae 12' with outwardly facing pleats 16' of a different but uniform pitch or having one or two nonuniform pitches. This execution may be combined with the three laminae laminate 10, discussed above, so that a laminate 10' having two pleated outboard laminae 12' and a central unpleated lamina results.

Another feasible variation is to utilize elastically extensible laminae 12 and particularly 14, extensible perpendicular to the pleats 16, so that the resulting laminate 10 has elastic properties and may be stretched. A preferred elastically extensible embodiment has an unpleated elastomeric lamina 14 joined to a pleated lamina 12. The unpleated lamina 14 may be stretched either before or after being joined to the pleated lamina 12. Another preferred elastically extensible embodiment has two outboard pleated laminae 12' and a central elastomeric unpleated lamina.

If the unpleated lamina 14 is stretched in the machine direction prior to bonding, or if the pleated and unpleated laminae 12 and 14 or both pleated laminae 12' are extensible in the direction generally parallel to the pleats 16, a laminate 10 or 10' having bielastic properties may be produced and stretched parallel or perpendicular to the pleats 16. It will be further apparent, that other variations in the method disclosed herein and laminate 10 produced hereby may be made without departure from the spirit and scope of this invention and are particularly suited for use with absorbent articles.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 80, shown in FIG. 8. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

Figure 8:
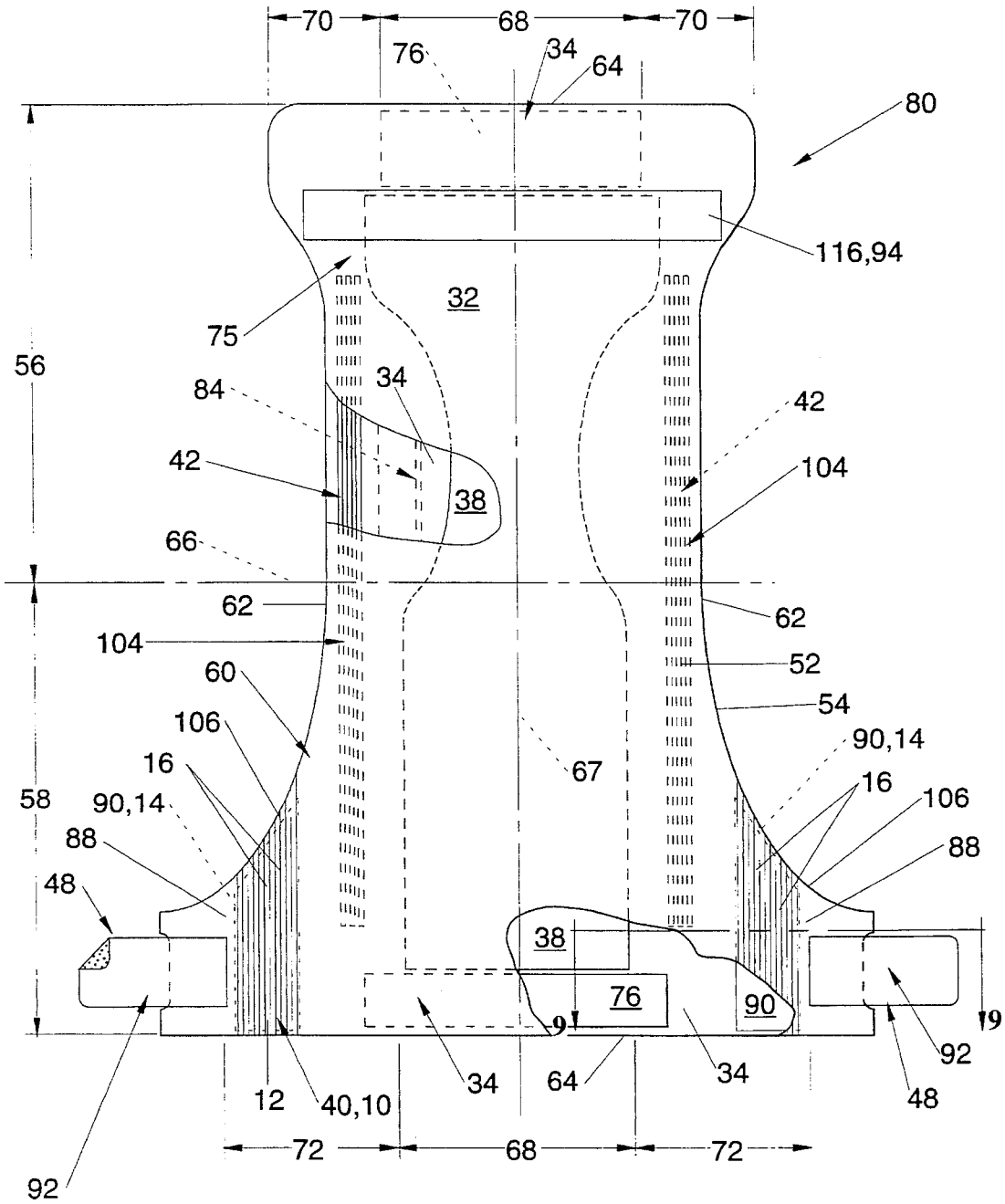
FIG. 8 is a plan view of a disposable diaper embodiment of the present invention having portions cut-away to reveal underlying structure, the outer surface of the diaper facing the viewer.

FIG. 8 is a plan view of the disposable diaper 80 of the present invention in its flat-out, uncontracted state (i.e., with elastic induced contraction pulled out except in the side panels wherein the elastic is left in its relaxed condition) with the portion of the diaper 80 which faces away from the wearer, the outer surface 52, facing the viewer. As shown in FIG. 8, the diaper 80 comprises a chassis 75 comprising a containment assembly 32; elasticized side panels 40; elasticized leg cuffs 42; elasticized waistbands 44; and a fastening system 48.

The containment assembly 32 of the disposable diaper 80 preferably comprises a liquid pervious topsheet 34, a liquid impervious backsheet 36 joined with the topsheet 34, and an absorbent core 38 positioned between the topsheet 34 and the backsheet 36. While the topsheet, the absorbent core, the backsheet and the elastic members may be assembled in a variety of well known configurations, preferred disposable diaper configurations are described in U.S. Pat. No. 3,860,003 entitled "Contractible Side Portions For Disposable Diapers" which issued to K. B. Buell on Jan. 14, 1975; U.S. Pat. No. 4,695,278 entitled "Absorbent Article Having Dual Cuffs" which issued to Lawson on Sep. 22, 1987; U.S. Pat. No. 4,938,755 entitled "Absorbent Article Having A Containment Pocket" which issued to Foreman on Jul. 3, 1990; and which patents are incorporated herein by reference.

The inner surface 54 of the diaper 80 comprises that portion of the diaper 80 which is positioned adjacent to the wearer's body during use (i.e., the inner surface 54 generally is formed by at least a portion of the topsheet 34 and other components joined to the topsheet 34). The outer surface 52 comprises that portion of the diaper 80 which is positioned away from the wearer's body (i.e., the outer surface 52 generally is formed by at least a portion of the backsheet 36 and other components joined to the backsheet 36). The first waist region 56 and the second waist region 58 extend, respectively, from the end edges 64 of the periphery 60 to the lateral centerline 66 of the diaper 80. The waist regions each comprise a central region 68 and a pair of side panels which typically comprise the outer lateral portions of the waist regions. The side panels positioned in the first waist region 56 are designated 70 while the side panels in the second waist region 58 are designated 72. (In the discussion that follows, unless otherwise noted, the diaper 80 will comprise a pair of side panels in each waist region. While it is not necessary that the pairs of side panels or each side panel be identical, they are preferably mirror images one of the other.) In a preferred embodiment of the present invention, the side panels 72 positioned in the second waist region 58 are elastically extensible in the lateral direction (i.e., elasticized side panels 40). (The lateral direction (x direction or width) is defined as the direction parallel to the lateral centerline 66 of the diaper 80; the longitudinal direction (y direction or length) being defined as the direction parallel to the longitudinal centerline 67; and the axial direction (Z direction or thickness) being defined as the direction extending through the thickness of the diaper 80.)

FIG. 8 shows a preferred embodiment of the diaper 80 in which the topsheet 34 and the backsheet 36 have length and width dimensions generally larger than those of the absorbent core 38. The topsheet 34 and the backsheet 36 extend beyond the edges of the absorbent core 38 to thereby form the periphery 60 of the diaper 80. The periphery 60 defines the outer perimeter or, in other words, the edges of the diaper 80. The periphery 60 comprises the longitudinal edges 62 and the end edges 64.

The containment assembly 32 of the diaper 80 is shown in FIG. 8 as comprising the chassis 75 of the diaper 80. The containment assembly 32 comprises at least an absorbent core 38 and preferably an outer covering layer comprising the topsheet 34 and the backsheet 36. When the absorbent article comprises a separate holder and a liner, the containment assembly 32 generally comprises the holder and the liner (i.e., the containment assembly 32 comprises one or more layers of material to define the holder while the liner comprises an absorbent composite such as a topsheet, a backsheet, and an absorbent core.) For unitary absorbent articles, the containment assembly 32 comprises the main structure of the diaper with other features added to form the composite diaper structure. Thus, the containment assembly 32 for the diaper 80 generally comprises the topsheet 34, the backsheet 36, and the absorbent core 38.

The absorbent core 38 may be any absorbent means which is generally compressible, conformable, non-irritating to the wearer's skin, and capable of absorbing and retaining liquids such as urine and other certain body exudates.

The absorbent core 38 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 38 should, however, be compatible with the design loading and the intended use of the diaper 80. Further, the size and absorbent capacity of the absorbent core 38 may be varied to accommodate wearers ranging from infants through adults.

A preferred embodiment of the diaper 80 has an asymmetric, modified T-shaped, absorbent core 38 having ears in the first waist region 56 but a generally rectangular shape in the second waist region 58. This configuration allows wider elasticized side panels 40 in the second waist region 58. An exemplary absorbent structure for use as the absorbent core 38 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. The absorbent core 38 is preferably the commercially successful absorbent member described in U.S. Pat. No. 4,834,735, entitled "High Density Absorbent Members Having Lower Density and Lower Basis Weight Acquisition Zones", issued to Alemany and Berg on May 30, 1989. Each of these references are incorporated herein by reference.

The backsheet 36 is positioned adjacent the absorbent core 38 and is preferably joined thereto by attachment means (not shown) such as those well known in the art. For example, the backsheet 36 may be secured to the absorbent core 38 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minnesota and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 36 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 36 prevents the exudates absorbed and contained in the absorbent core 38 from wetting articles which contact the diaper 80 such as bedsheets and undergarments. The backsheet 36 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils).

Preferred polymeric films for use as the backsheet contain a high content of linear low density polyethylene. Particularly preferred materials for the backsheet include blends comprised of about 45–90% linear low density polyethylene and about 10–55% polypropylene. Exemplary films for use as the backsheet of the present invention are manufactured by Tredegar Industries, Inc. of Terre Haute, Indiana under the designation RR8220 blend for blown films and RR5475 blend for cast films. The backsheet 36 is preferably embossed (typically, to a caliper of about 0.127 mm (5.5 mils)) and/or matte finished to provide a more clothlike appearance. Further, the backsheet 36 may permit vapors to escape from the absorbent core 38 ( i.e., breathable) while still preventing exudates from passing through the backsheet 36.

The size of the backsheet 36 is dictated by the size of the absorbent core 38 and the exact diaper design selected. In a preferred embodiment, the backsheet 36 has a modified hourglass shape extending beyond the absorbent core 38 a minimum distance of at least about 1.3 cm to about 2.5 cm (about 0.5 to about 1.0 inch) around the entire diaper periphery 60. Preferably, the backsheet 36 is much wider than the absorbent core 38 in the second waist region 58 so that the side panels 72 in the second waist region 58 are generally wider in the lateral direction than the side panels 70 in the first waist region 56.

The topsheet 34 is positioned adjacent the absorbent core 38 and is preferably joined thereto and to the backsheet 36 by attachment means (not shown) such as those well known in the art. Suitable attachment means are described with respect to joining the backsheet 36 to the absorbent core 38. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. As used herein, the term "joined" also encompasses configurations whereby two discrete elements are affixed to each other, and configurations whereby two elements are unitary (i.e., each element may comprise discrete components affixed thereto, but the two elements comprise at least one common component). In a preferred embodiment of the present invention, the topsheet 34 and the backsheet 36 are joined directly to each other in the diaper periphery 60 and are indirectly joined together by directly joining them to the absorbent core 38 by the attachment means (not shown).

The topsheet 34 is compliant, soft feeling, and nonirritating to the wearer's skin. Further, the topsheet 34 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 34 is made of a hydrophobic material to isolate the wearer's skin from liquids contained in the absorbent core 38.

There are a number of manufacturing techniques which may be used to manufacture the topsheet 34. For example, the topsheet 34 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Massachusetts under the designation P-8.

The diaper 80 preferably further comprises elasticized leg cuffs 42 for providing improved containment of liquids and other body exudates. Each elasticized leg cuff 42 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. While each elasticized leg cuff 42 may be configured so as to be similar to any of the leg bands, side flaps, barrier cuffs, or elastic cuffs described above, as shown in FIG. 8 and FIG. 9, it is preferred that each elasticized leg cuff 42 comprise at least an inner barrier cuff 84 as described in the above-referenced U.S. Pat. No. 4,909,803. In a preferred embodiment as shown in FIG. 8, the elasticized leg cuff 42 additionally comprises an elastic gasketing cuff 104 such as described in the above-referenced U.S. Pat. No. 4,695,278. Suitable leg cuffs may also comprise the stretch laminate discussed herein with respect to the elasticized side panels 40. The stretch laminate 10 may be formed separately from the containment assembly 32 and then affixed to the containment assembly 32 to form an elasticized leg cuff 42 (i.e., the inner barrier cuff 84, the gasketing cuff 104, or both). Alternatively, the stretch laminate 10 may form a unitary elasticized leg cuff 42. To form a unitary elasticized leg cuff 42 comprising a stretch laminate 10, portions of the containment assembly 32 (e.g., the topsheet, the backsheet, or both) which extend into the leg cuff area are pleated to form at least one pleated lamina 12 which is bonded to an elastomeric lamina 14 such that the resulting laminate 10 will be elastically extensible in at least one direction.

The diaper 80 further comprises ,an elasticized waistband 44 disposed adjacent the end edge 64 of the diaper 80 in the first waist region 56. The waistband of the diaper 80 is that portion which is intended to be placed adjacent the wearer's waist. The elasticized waistband 44 provides a member that maintains a defined area coverage, contacts the wearer's waist, and is elastically extensible in at least the lateral direction so as to dynamically fit against the waist of the wearer and to dynamically conform to the waist of the wearer so as to provide improved fit.

While the elasticized waistband 44 can comprise a separate element affixed to the containment assembly 32 of the diaper 80, the waistband is preferably an extension of other elements of the diaper 80 such as the topsheet 34 or the backsheet 36 or both and an elastomeric material joined thereto. Disposable diapers are often constructed so as to have two elasticized waistbands; one positioned in the first waist region 56 and one positioned in the second waist region 58. As discussed herein, the diaper 80 at least has an elasticized waistband 44 disposed in at least the central region 68 of the first waist region 56. Preferably, as shown in FIG. 8, another elasticized waistband is disposed in the second waist region 58, preferably between the elasticized side panels 40.

The elasticized waistband 44 may be constructed in a number of different configurations including those described herein with respect to the stretch laminates 10 of the elasticized side panels 40. The stretch laminate 10 may be formed separately from the containment assembly 32 and then affixed to the containment assembly 32 to form an elasticized waistband 44. Alternatively, the stretch laminate 10 may form a unitary elasticized waistband 44. To form a unitary elasticized waistband 44, portions of the containment assembly 32 which extend into the waist region of the chassis 75 (e.g., portions of the topsheet 34, the backsheet 36, or both, which extend into the first waist region 56, the second waist region 58, or both) are pleated to form at least one pleated lamina 12 which is bonded to an elastomeric lamina 14 such that the resulting laminate 10 is elastically extensible in at least one direction.

In a preferred embodiment of the present invention shown in FIG. 8, the elasticized waistband 44 comprises an elastic waistband member 76 interposed between the topsheet 34 and the backsheet 36 and operatively associated with either or both the topsheet 34 and the backsheet 36 to gather the first waist region 56 of the diaper 80. An example of such an elasticized waistband for use herein is the elasticized waistband disclosed in U.S. Pat. No. 4,515,595 entitled "Disposable Diapers With Elastically Contractible Waistbands", which issued to Kievit and Osterhage on May 7, 1985, and which patent is incorporated herein by reference. Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates or mechanically stretched pretensioned stretch laminates; and elastic strands made from rubber, LYCRA, or other materials. In a preferred embodiment, the elastic waistband member 76 comprises a Kraton based elastomer film, which films are available from the Exxon Chemical Company, 5200 Bay Way Drive, Baytown, Texas 77520. Other embodiments of preferred constructions for the elasticized waistband are the elastic waist features described in commonly assigned, co-pending, U.S. patent application Ser. No. 07/750,775, filed Aug. 22, 1991 in the name of K. B. Buell et al., "Absorbent Article With Dynamic Elastic Waist Feature Having A Predisposed Resilient Flexural Hinge"; the specification and drawings of which are incorporated herein by reference.

In an alternative embodiment, the elasticized waistband in the second waist region 58 (or in the first waist region 56 if elasticized side panels are disposed therein) and the elasticized side panels 40 can be formed by securing a single piece of elastomeric material to the diaper 80 in both the side panels 72 and the central region 68 of the second waist region 58. Thus, the elasticized waistband 44 and the elasticized side panels 40 can be formed from the same piece of material to form a unitary structure. An example of such an elasticized waistband/side panel configuration is disclosed in the hereinbefore referenced U.S. Pat. No. 4,887,067 issued to Wood, et al. on Aug. 15, 1989, and which patent is incorporated herein by reference.

The diaper 80 is further provided with a fastening system 48 for forming a waist closure. The fastening system 48 maintains the first waist region 56 and the second waist region 58 in an overlapping configuration to maintain the diaper on the wearer.

The diaper 80 may comprise any type of fastening system 48 that is well known in the art. As shown in FIG. 8, the fastening system 48 comprises a first fastening component, tape tab 92, attached to the side edges 62 of the diaper 80 in the second waist region 58. The fastening system 48 preferably also comprises a complementary second fastening component, landing member 94, engageable with the first fastening component. An exemplary fastening system 48 wherein the first and second fastening components each comprise mechanical closure elements comprising hook and loop fastening materials is disclosed in U.S. Pat. No. 4,869,724 entitled "Mechanical Fastening Systems With Adhesive Tape Disposal Means For Disposable Absorbent Articles" issued to Scripps on Sep. 26, 1989. Fastening systems utilizing mechanical closure elements are also disclosed in U.S. Pat. No. 4,846,815 entitled "Disposable Diaper Having An Improved Fastening Device" issued to Scripps on Jul. 11, 1989; and U.S. Pat. No. 4,894,060 entitled "Disposable Diaper With Improved Hook Fastener Portion" issued to Nestegard on Jan. 16, 1990. A fastening system having combination adhesive/mechanical closure elements is described in U.S. Pat. No. 4,946,527 entitled "Pressure-Sensitive Adhesive Fastener And Method of Making Same" issued to Battrell on Aug. 7, 1990. Each of these patents are incorporated herein by reference. A disposable diaper having a two point fastening system is described in U.S. patent application Ser. No. 07/714,476, entitled "Absorbent Article with Fastening System Providing Dynamic Elasticized Waistband Fit", filed Jun. 13, 1991 in the name of Weil et al., which patent application is incorporated herein by reference. In a preferred embodiment of the present invention as is shown in FIG. 8, the fastening system 48 comprises an adhesive tape tab fastening system comprising a tape tab 92 having an adhesive attachment layer 96 and a landing member 94 comprising a reinforcing strip 116 joined to the backsheet 36. Examples of such adhesive tape tab fastening systems are disclosed in U.S. Pat. No. 3,848,594 entitled "Tape Fastening System for Disposable Diaper" issued to Buell on Nov. 19, 1974; and the adhesive tape tabs, reinforcing strip, and indicia means disclosed in U.S. Pat. No. B1 4,662,875 entitled "Absorbent Article" issued to Hirotsu and Robertson on May 5, 1987. Each of these patents are incorporated herein by reference. The reinforcing strip 116 of the landing member 94 may comprise any of a number of configurations and materials secured to the backsheet 36 of the diaper 80. The reinforcing strip 116 is preferably a separate member secured to the backsheet 36 to form a portion of the outer surface 52 of the diaper 80. A preferred reinforcing strip 116 comprises a sheet of biaxially oriented polypropylene film.

In a preferred embodiment, the diaper also comprises elasticized side panels 40 disposed in the second waist region 58. (As used herein, the term "disposed" is used to mean that an element(s) of the diaper is formed (joined and positioned) in a particular place or position as an unitary structure with other elements of the diaper or as a separate element joined to another element of the diaper.) The elasticized side panels 40 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. Further, the elasticized side panels 40 develop and maintain wearing forces (tensions) that enhance the tensions developed and maintained by the fastening system 48 to maintain the diaper 80 on the wearer and enhance the waist fit. The elasticized side panels 40 further provide more effective application of the diaper 80 since even if the diaperer pulls one elasticized side panel 40 farther than the other during application (asymmetrically), the diaper 80 will "self-adjust" during wear. While the diaper 80 of the present invention preferably has the elasticized side panels 40 disposed in the second waist region 58; alternatively, the diaper 80 may be provided with elasticized side panels 40 disposed in the first waist region 56 or in both the first waist region 56 and the second waist region 58.

Figure 9:
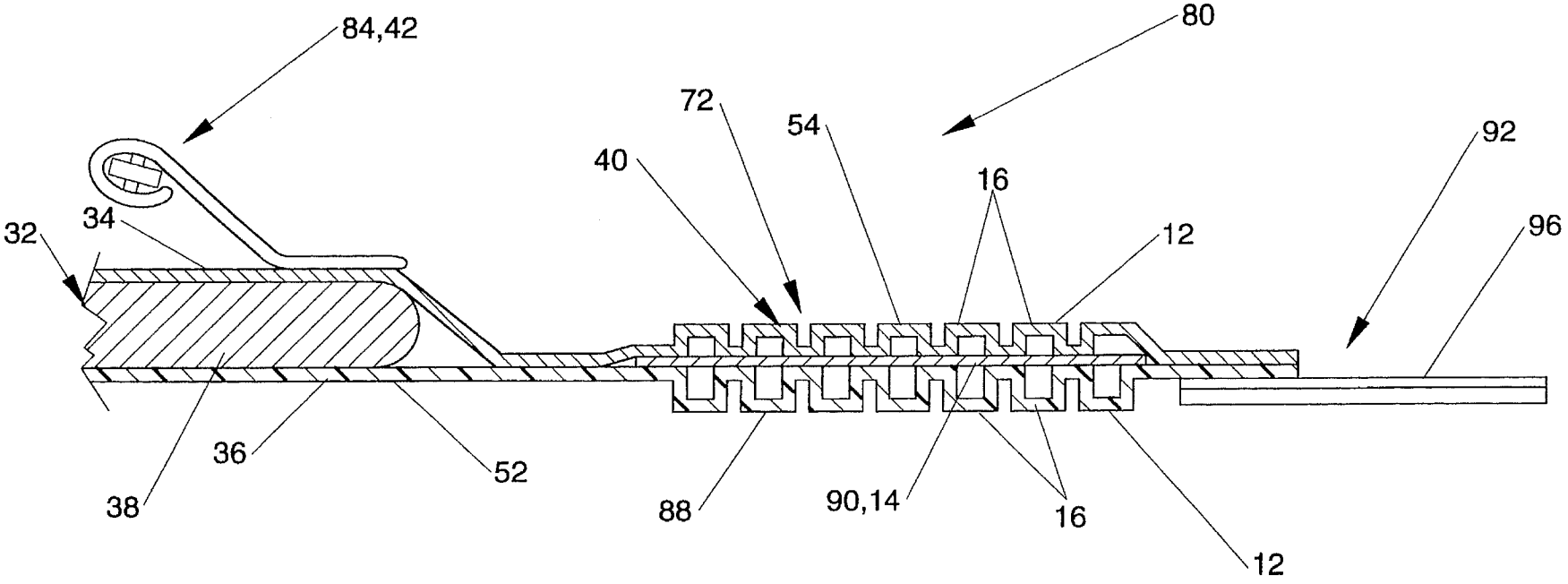
FIG. 9 is an inverted fragmentary sectional view of the disposable diaper shown in FIG. 8 taken along section line 9–9 of FIG. 8.

As shown in FIG. 8 and FIG. 9, each elasticized side panel 40 comprises an ear flap 88 and an elastic side panel member 90 operatively associated therewith. Each ear flap 88 comprises that portion of the side panel 72 that extends laterally outwardly from and along the side edge of the absorbent core 38 to the longitudinal edge 62 of the diaper 80. The ear flap 88 generally extends longitudinally from the end edge 64 of the diaper 80 to the portion of the longitudinal edge. 62 of the diaper 80 that forms the leg opening (this segment of the longitudinal edge 62 being designated as leg edge 106). In a preferred embodiment of the present invention, each ear flap 88 in the second waist region 58 is formed by the portions of the topsheet 34 and the backsheet 36 that extend beyond the side edge of the absorbent core 38.

In a preferred embodiment of the present invention, the elastic side panel members 90 are operatively associated with the diaper 80 in the ear flaps 88, preferably between the topsheet 34 and the backsheet 36, so that the elastic side panel members 90 allow the elasticized side panels 40 to be elastically extensible in the lateral direction (laterally elastically extensible). As used herein, the term "elastically extensible" means a segment or portion of the diaper that will elongate in at least one direction (preferably the lateral direction for the side panels and the waistbands) when tensional forces (typically lateral tensional forces for the side panels and the waistbands) are applied, and will return to about its previous size and configuration when the tensional forces are removed. Generally, elastomeric materials useful in the present invention will contractively return to at least about 75% of their original configuration within about 5 seconds or less upon stretch and immediate release thereof (i.e., a "snappy" elastic).

The method and apparatus discussed hereinbefore with respect to forming a laminate 10 comprising at least one pleated lamina, are used to operatively associate the elastic side panel member 90, or elastomeric laminate 14, with the ear flap 88 to form an elastic side panel 40.

The elastic side panel member 90 is operatively associated in the ear flap 88 by longitudinally pleating the ear flap 88 portions of the diaper web (e.g., the topsheet 34, the backsheet 36, or both) to form a pleated lamina 12 and joining the elastic side panel member 90 to the pleated lamina 12 of the ear flap 88. The elasticized side panel is thus formed into a stretch laminate 10. (Alternatively, the elastic side panel member could be operatively associated in a tensioned condition with the pleated lamina of the ear flap 88; although this is not as preferred as operatively associating the elastic side panel member in an untensioned condition with the pleated lamina of the ear flap 88;). As used herein, the term stretch laminate refers to a laminate comprised of at least two plies of material which are secured to one another along at least a portion of their coextensive surfaces; one of the plies comprising a material which is stretchable and elastomeric (i.e., it will return substantially to its untensioned dimensions after an applied tensile force has been released) and a second ply which is not necessarily elastomeric, but is pleated. The resulting stretch laminate is thereby rendered elastically extensible, at least up to the width of the pleated lamina in its unpleated condition.

In the preferred embodiment of the present invention shown in FIG. 9, the ear flap 88 will comprise portions of the topsheet 34 and backsheet 36. The ear flap portions of the topsheet 34 and backsheet 36 will be pleated to form two pleated laminae 12 having oppositely facing machine-direction oriented pleats 16. The two pleated laminae 12 (the ear flap portions of the topsheet 34 and the backsheet 36) having oppositely facing machine-direction oriented pleats 16, are joined to an elastomeric lamina 14 (elastic side panel member 90) using the apparatus 20' illustrated in FIG. 5 to form a stretch laminate 10 (elastic side panel 40).

The pleats of the topsheet 34 and the backsheet 36 are formed using any means well known in the art as described hereinbefore. The pleated portions of the topsheet 34 and backsheet 36 are provided and confluently passed through the nip of the apparatus 20' with the elastic side panel member 90 therebetween. The pleated surfaces of the topsheet 34 and the backsheet 36 facing outwardly from the elastic side panel member 90 and facing oppositely from each other. The pleats 16 of the topsheet 34 and the backsheet 36 are matched in geometry to the circumferential grooves 26' of the rolls 22' and transversely registered as described hereinbefore. The pleated portions of the topsheet 34 and backsheet 36 are then joined to the elastic side panel member 90, either adhesively or autogenously as described above.

Although the topsheet 34 and backsheet 36 are described as having pleats 16 only in the portions which extend into the ear flap 88, it should be understood that the topsheet 34 and backsheet 36 can be pleated throughout their entire areas. It should also be understood that the entire containment assembly 32 of the diaper 80 may be formed of the stretch laminate 10 described herein. Although FIG. 9 shows the pleated lamina 12 having pleats of uniform pitch, it should be understood that the pitch of the pleats 16 of the pleated lamina 12 may also be non-uniform.

The elastic side panel members 90 may take on a number of different sizes, shapes, configurations and materials. For example, the elasticized side panels 40 may be formed from one or a plurality of elastic side panel members 90 operatively associated in each ear flap 88; the elastic side panel members may have varying widths and lengths; or the elastic side panel members may comprise relatively narrow strands of elastomeric material or a larger area elastomeric patch. Suitable elastomeric materials for use as the elastic side panel members 90, i.e., the elastomeric lamina 14, include Kraton based elastomer films which are available from the Exxon Chemical Company, 5200 Bay Way Drive, Baytown, Texas 77520.

As shown in FIG. 8, the elastic side panel member 90 comprises a patch of elastomeric material (elastomeric patch) that preferably extends through the length of the ear flap 88 in the second waist region 58. Although the elastic side panel member 90 may longitudinally extend through only a portion of the length of the ear flap 88, it is preferred that the elastic side panel member 90 longitudinally extend through the entire length of the ear flap 88.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing a disposable absorbent article having portions which are elastically extensible in at least a first direction, said method comprising the steps of:

providing a chassis, said chassis comprising:

a liquid pervious topsheet, a liquid impervious backsheet joined with said topsheet, and an absorbent core positioned between said topsheet and said backsheet;

providing a first lamina joined to said chassis, said first lamina having pleats, said pleats being oriented in a second direction;

providing at least one elastomeric lamina in face to face relation with at least a portion of said pleats of said first lamina;

providing two circumferentially grooved rolls, a first roll and a second roll, having mutually parallel axes and defining a nip therebetween, at least said first roll having a plurality of circumferential grooves and lands intermediate said grooves, said grooves being oriented in said second direction;

passing said first lamina and said elastomeric lamina in face to face relation through said nip, such that said pleats of said first lamina face said grooves of said first roll;

transversely registering the pleats of said first lamina with said grooves of said first roll;

pressing said rolls together about a the plane generally perpendicular to and connecting the axes of said rolls so that said first lamina contacts said elastomeric lamina at a position corresponding to said lands; and bonding said first lamina to said elastomeric lamina at said positions of contact.

2. The method of claim 1, wherein at least said first lamina comprises a thermoplastic material, said first roll has at least one generally radially oriented upstanding protrusion, and wherein said first lamina is autogenously bonded to said elastomeric lamina.

3. The method of claim 2, wherein said first lamina and said elastomeric lamina pass through said nip at a velocity differential of at least about 2%.

4. The method of claim 2, wherein said rolls are pressed about the plane generally perpendicular to and connecting the axes of said rolls so that a pressure of about 42,200,000 kilograms per square meter to about 56,200,000 kilograms per square meter is obtained on at least one roll.

5. The method of claim 4, further comprising the step of heating at least one of said rolls to a temperature sufficient to effect joining of said first lamina and said elastomeric lamina.

6. The method of claim 1, wherein said grooves of said first roll have a nonuniform pitch.

7. The method of claim 1, wherein said first lamina is a separate element affixed to said chassis.

8. The method of claim 1, wherein said first lamina is an extension of said topsheet or said backsheet.

9. A method for manufacturing a disposable absorbent article having portions which are elastically extensible in at least a first direction, said method comprising the steps of:

providing a chassis, said chassis comprising:

a liquid pervious topsheet, a liquid impervious backsheet associated with said topsheet, an absorbent core positioned between said topsheet and said backsheet, and at least two ear flaps joined to said topsheet and/or said backsheet, each of said ear flaps comprising a first lamina and a second lamina, said first lamina and said second lamina having pleats, said pleats of said second lamina being substantially mutually parallel with and outwardly facing from said pleats of said first lamina and said pleats being oriented in a second direction;

providing at least one elastomeric lamina in face to face relation with at least a portion of said pleats of said first lamina;

providing two rolls, a first roll and a second roll, having mutually parallel axes and defining a nip therebetween, said first roll and said second roll having a plurality of circumferential grooves and lands intermediate said grooves, said grooves being oriented in said second direction;

passing said first lamina and said second lamina through said nip with said elastomeric lamina positioned between said first lamina and said second lamina, such that said pleats of said first lamina face said grooves of said first roll and said pleats of said second lamina face said grooves of said second roll;

transversely registering the pleats of said first lamina with said grooves of said first roll and transversely registering the pleats of said second lamina with said grooves of said second roll;

pressing said rolls together about a plane generally perpendicular to and connecting the axes of said rolls so that said first lamina and said second lamina contact said elastomeric lamina at a position corresponding to said lands; and bonding said first lamina and said second lamina to said elastomeric lamina at said positions of contact.

10. The method of claim 9, wherein at least one of said first lamina, said second lamina, and said elastomeric lamina comprises a thermoplastic material, at least one of said rolls has at least one generally radially oriented upstanding protrusion, and wherein said first lamina and said second lamina are autogenously bonded to said elastomeric lamina.

11. The method of claim 10, wherein said first lamina and said second lamina pass through said nip at a velocity differential of at least about 2%.

12. The method of claim 10, wherein said rolls are pressed about the plane generally perpendicular to and connecting the axes of said rolls so that a pressure of about 42,200,000 kilograms per square meter to about 56,200,000 kilograms per square meter is obtained on at least one roll.

13. The method of claim 12, further comprising the step of heating at least one of said rolls to a temperature sufficient to effect joining of said laminae.

14. The method of claim 9, wherein said ear flap is a separate element joined to said chassis.

15. The method of claim 9, wherein said first lamina comprises a portion of said topsheet and said second lamina comprises a portion of said backsheet.

* * * * *